Figure 1:
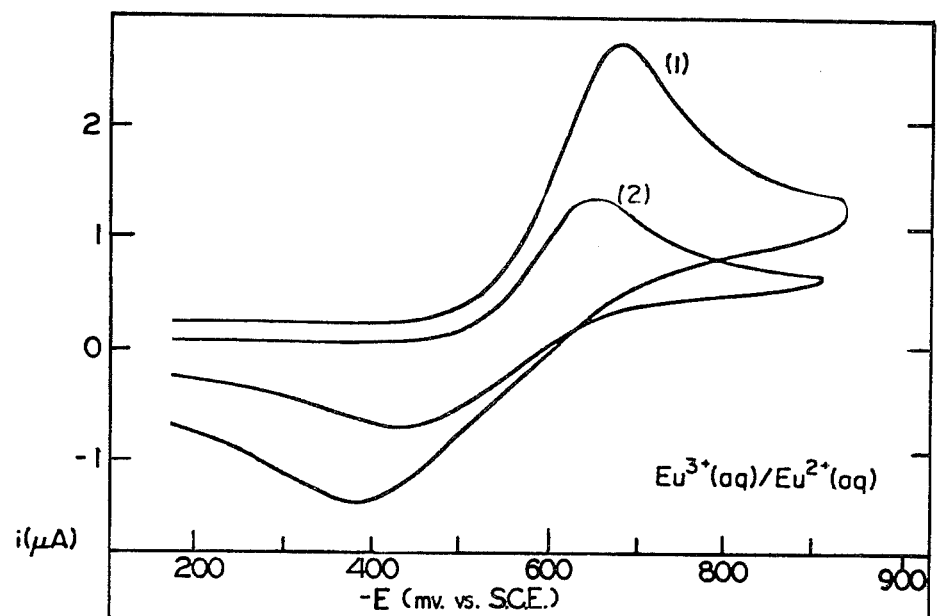

United States Patent [19]

Gansow et al.

[11] 4,257,955

[45] Mar. 24, 1981

[54] LANTHANIDE RARE EARTH SERIES CRYPTATE COMPOUNDS AND PROCESS FOR THE PREPARATION OF METAL CRYPTATES IN GENERAL

[75] Inventors: Otto A. Gansow, East Lansing, Mich.; Kelly B. Triplett, Stamford, Conn.

[73] Assignee: Board of Trustees, Michigan State University, East Lansing, Mich.

[21] Appl. No.: 949,216

[22] Filed: Oct. 6, 1978

[51] Int. Cl.$^3$ .................... C07F 5/00; C07F 15/06; C07F 15/04; C07F 15/02; C07F 13/00; C07F 11/00; C07F 9/00; C07F 7/28
[52] U.S. Cl. .................... 260/338; 260/340.3
[58] Field of Search .................... 260/338, 340.3

[56] References Cited

U.S. PATENT DOCUMENTS

| | | | |
|---|---|---|---|
| 3,686,225 | 8/1972 | Pedersen | 260/340.3 |
| 3,763,188 | 10/1973 | Krespan | 260/338 |
| 3,888,877 | 6/1975 | Lehn | 260/338 |
| 3,966,766 | 6/1976 | Lehn | 260/338 |
| 3,997,563 | 12/1976 | Dale | 260/338 |
| 4,025,523 | 5/1977 | Steiner et al. | 260/338 |

FOREIGN PATENT DOCUMENTS 2348449  8/1978  Fed. Rep. of Germany .

OTHER PUBLICATIONS

V. M. Loyala et al., Jour. Am. Chem. Soc., vol. 97, No. 25, (Dec. 10, 1975), pp. 7382-7383.
O. A. Gansow et al., Jour. Am. Chem. Soc., vol. 99, No. 21, (Oct. 12, 1977), pp. 7087-7089.
F. Alan Hart et al., J. C. S. Chem. Comm., (Jul. 1978), pp. 549-550.
J. M. Lehn et al., Jour. Am. Chem. Soc., vol. 97, No. 23, (Nov. 12, 1975), pp. 6700-6707.
Joseph M. Ceraso et al., Jour. Phys. Chem., vol. 81, No. 8, (1977), pp. 760-766.
Kirk-Othmer, vol. 4, pp. 390-391.
J. M. Lehn, Structural Bonding, Berlin, vol. 16, (1973), pp. 7-25.
J. M. Lehn, Pure and Applied Chem., vol. 49, (1977), pp. 857-870.
Chemical Abstracts, vol. 66, (1967), 101187j.

*Primary Examiner*—Norma S. Milestone
*Attorney, Agent, or Firm*—Ian C. McLeod

[57] ABSTRACT

Novel lanthanide rare earth series cryptate coordination compounds or complexes are described. The compounds are highly kinetically inert in aqueous solution to dissociation of the complexes as a function of time. The compounds are particularly useful as relaxation agents in NMR spectra because of their stability in water or polar organic solvents and are also useful in electrochemistry, synthesis and medicine. A process for the preparation of metal cryptate coordination compounds in general is also described.

8 Claims, 2 Drawing Figures

LANTHANIDE RARE EARTH SERIES CRYPTATE COMPOUNDS AND PROCESS FOR THE PREPARATION OF METAL CRYPTATES IN GENERAL

BACKGROUND OF THE INVENTION

1. Field of the Invention

The present invention relates to lanthanide rare earth series cryptate salts. In particular the present invention relates to trivalent lanthanide cryptate salts which are highly stable in polar solvents, such as water. The invention also relates to a novel process for forming metal cryptate coordination compounds in general.

2. Description of the Prior Art

The prior art has described the preparation of mono- and divalent alkali metal and alkaline earth metal cryptate coordination compounds in J. Phys. Chem. 81, 760 (1977); J. Am. Chem. Soc. 97, 7382 (1975) Structural Bonding Berlin 16,2 (1973) and J. Am. Chem. Soc. 97, 6700 (1975). Such metal cryptate compounds are relatively labile in aqueous solution and exchange with non-encryptated or aquated ions or merely dissociate over relatively short periods of time (a few minutes or less).

SUMMARY OF THE INVENTION

The present invention relates to lanthanide rare earth series cryptate coordination compounds wherein the cryptand ligand has the structural formula:

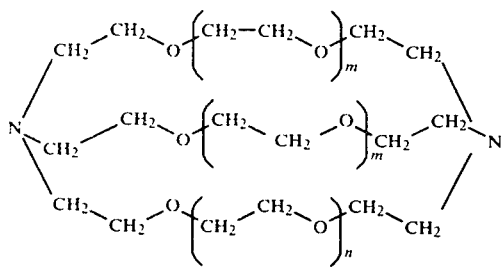

wherein m is 1 and n is 0 (referred to herein as 2:2:1) or wherein m and n are both 1 (referred to herein as 2:2:2) or have the structural formula:

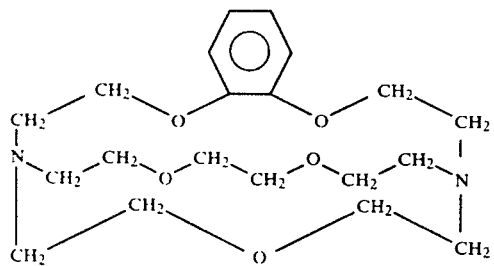

referred to herein as 2:2:1. These compounds are characterized as lanthanide rare earth cryptates of polyoxadiazamacrobicyclic polyether cryptand ligands with repeating oxyethylene groups forming the polyether. The lanthanide cryptate coordination compounds are highly inert in aqueous solution.

The present invention also relates to the process for forming a metal cryptate coordination compound which comprises: providing an inorganic metal salt to be encryptated with a polyoxadiazamacrobicyclic polyether cryptand ligand in polar organic solvent; and separating the encryptated metal salt from the solvent. The metal salts can be alkali metal, alkaline earth metal, lanthanide or actinide series salts. The metal salt in most instances should be anhydrous.

OBJECTS

It is thus an object of the present invention to provide unique "inert" lanthanide cryptate coordination complexes, particularly when they are dissolved in water or other polar solvents. It is also an object of the present invention to provide a method for preparing metal cryptates in general. These and other objects will become apparent by reference to the following description and to the drawing.

IN THE DRAWING

Figure 2:
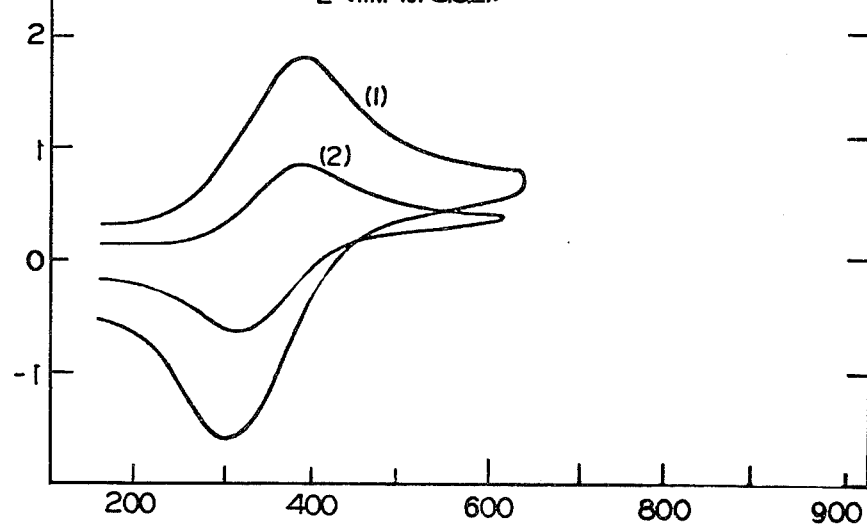

FIGS. 1 and 2 are cathodic-anodic cyclic europium voltammograms where FIG. 1 is of a 0.4 mM $Eu^{3+}$ in water with 0.5 M sodium perchlorate at pH 2 and FIG. 2 is of 0.35 mM $Eu(2:2:1)^{3+}$ cryptate in water with 0.5 M sodium perchlorate at pH 7. The electrode area is 0.032 $cm^2$. The sweep rates were: (1) 200 mV per second: (2) 50 mV per second.

SPECIFIC DESCRIPTION

The lanthanide series of rare earth metals are well known. The usual ionic form is trivalent; however, divalent reduced forms are also known for europium and ytterbium. Some of the members of this series are radioactive and are used as tracers for medicines and for other diagnostic test purposes.

The cryptates described herein have been found to form unexpectedly stable and inert coordination complexes in coordination No. VII with lanthanide rare earth series elements. These elements have effective ionic radii in coordination number VII between 0.85 and 1.10 1 angstroms which are in the same range as divalent calcium and monovalent sodium ionic radii which are about 1 angstrom. In examining the prior art compounds it was found that the divalent calcium cryptate was more stable to dissociation than the monovalent sodium cryptate. It was thought that possibly a series of substitutionally inert, thermodynamically stable cryptate coordination complexes could be prepared with the trivalent lanthanide series elements.

The cryptates are polyoxadiazamacrobicyclic polyether ligands. The polyether includes repeating oxyethylene groups $+CH_2-CH_2O+$. U.S. Pat. Nos. 3,966,766 and 3,888,877 describe other ligands of the same general class.

In general, the process of the present invention involves a reaction of essentially equimolar amounts of the cryptate ligand with an anhydrous lanthanide compound in an anhydrous polar organic solvent. The reaction is preferably conducted in a non-reactive atmosphere such as nitrogen. Anhydrous polar organic solvents include nitriles, ketones and esters which solvate the reactants and metal cryptate compound. The preferred solvent is acetonitrile, although acetone or ethyl acetate can be used.

The preparation of anhydrous metal salts is difficult. In order to accomplish this a dehydrating agent such as a tri-lower alkyl orthoformate, preferably the triethyl or methyl orthoformate, or propylene carbonate is dissolved in the polar organic solvent. The bound water in the salt reacts with the preferred dehydrating agents to form a lower alkyl alcohol and a lower alkyl formate in the solvent to effectively eliminate the water from the metal salt in situ.

The metal cryptate compounds upon formation are removed from the solvent by precipitation using a miscible second non-polar solvent which is a non-solvent for the cryptate compound. Ethers such as diethyl ether are preferred for this purpose along with cooling at refrigeration temperatures to induce precipitation. Recrystallization from the polar organic solvent can be used to further purify the metal cryptate compounds.

The reaction is conducted at room temperatures preferably between 75° and 81° C. Higher temperatures can be used as can lower temperatures so long as the metal cryptate compounds are formed and so long as the solvent remains essentially liquid.

The metal salts can include the alkali metal, alkaline earth metal, lanthanide and actinide and first row divalent d-transition metal series cations. The anions preferably include any stable inorganic anion including particularly nitrate, perchlorate or halides, particularly chloride or bromide. Other possible inorganic anions include carbonate, sulfate hydroxyl, phosphate thiocyanate and various other oxides of carbon, phosphorus or sulphur or hydrogens or organic ions such as carboxylates.

Various syntheses were used to produce crystalline samples as described in the following Examples I to IV.

EXAMPLE I

Preparation of Ln-cryptates $(NO_3)_3$ (where Ln is La, Ce, Pr).

Two-tenths millimole (0.2 mm) of cryptand (2:2:1, 2:2:2 or $2_B$:2:1) and 0.2 mm of hydrated lanthanide nitrate were taken together in a 100 ml round bottom side arm flask. The flask was evacuated, filled with dry nitrogen gas and placed in a preheated (60°-70° C.) oil bath. Next, 25 ml of dry acetonitrile was added to the flask and the stirring was started. After 2 hours of refluxing, the solution was filtered using high vacuum.

To the filtrate, ethyl ether, a miscible, non-polar solvent, was added dropwise until the solution was cloudy. The solution was refrigerated under a nitrogen atmosphere where the crystals of lanthanide cryptates grew and precipitated. The cryptates were filtered, washed with cold ether and dried for 2-3 hours using high vacuum. The yield of the cryptate compounds were in the range of 60-70%.

EXAMPLE II

Preparation of Ln-cryptates $(NO_3)_3$ (Ln-Nd, Sm, Eu, Gd, Tb, Dy, Ho, Er, Tm, Yb and Lu).

In this procedure, the hydrated metal nitrates were dehydrated in situ prior to complexation which was the preferred process step. A solution of 0.2 mm of hydrated metal nitrate, 2 ml of triethylorthoformate, as the dehydrating agent, and 25 ml of dry acetonitrile was stirred and refluxed for 5 hours. A solution of 0.2 mm of benzocryptand ($2_B$:2:1) in 5 ml of dry acetonitrile was added to the dehydrated metal salt solution. The stirring and refluxing was continued for another 4 hours (for Nd through Gd), 16 hours (for Tb, Dy) and 25 hours (for Ho through Lu). After cooling, the solution was filtered, and to the filtrate a ethyl ether was added dropwise to cloudiness. The mixture was refrigerated from which the solid cryptate salts precipitated. The solid was filtered and dried for 4-5 hours using high vacuum. In the case of Yb, the cryptate salt precipitates after 25 hours. This solid was filtered, washed with ether and dried.

The following Examples III and IV show the preferred process.

EXAMPLE III

Nitrates and Perchlorates (All of the lanthanides were prepared with this process except Pm which is radioactive).

In order to prepare these compounds, 0.343 millimoles of hydrated lanthanide salt was dissolved in a solution of 40 ml dry acetonitrile and 10 ml trimethyl orthoformate (TMOF). The solution was refluxed for 1 hour under dry nitrogen. A solution of 0.343 millimoles cryptand in 10 ml dry acetonitrile was then added and refluxing was continued for an additional 2-3 hours. Some precipitate may form upon addition of the ligand to the nitrate salts, especially for the heavier lanthanides, but all or most of this dissolved as refluxing continued. The solution was then cooled and filtered through a fine porosity frit to remove any precipitate that may be present. In general, no measurable amount of solid was obtained. The solution was concentrated to a volume of approximately 20 ml. Diethyl ether was added until the solution became turbid and was then stored in the freezer. After crystallization, the product was collected on a medium porosity filter, washed with ether and hexane, then dried 24 hours at 100° under vacuum in an Abderhalden$_{t.m.}$ heated drying apparatus in the presence of phosphorus pentoxide ($P_2O_5$).

EXAMPLE IV

Chlorides (All lanthanides were prepared with this process except Pm).

In order to prepare these compounds, 0.343 millimoles of hydrated lanthanide chloride was dissolved in a solution of 40 ml acetonitrile and 10 ml TMOF. The solution was refluxed one hour under dry nitrogen. A solution of 0.343 millimoles of cryptand in 10 ml dry acetonitrile was added, and a precipitate immediately formed. Most of this precipitate redissolved with the lighter lanthanides, but as the atomic weight of the lanthanide increased, the amount of insoluable precipitate increased until, in the case of Lu, almost all of the salt is removed from solution in this initial precipitate. Refluxing longer than three hours does not affect the amount of precipitate remaining, and eventually leads to discoloration of the solution. After cooling, the initial precipitate was filtered. The volume of the solution was reduced to approximately 20 ml. Diethyl ether was added until the solution became turbid and the solution was stored in the freezer. After crystallization, the product was collected on a medium porosity filter, washed with ether and hexane, then dried 24 hours at 100° under vacuum in an Abderhalden$_{t.m.}$ apparatus in the presence of $P_2O_5$.

The Pm cryptates can be prepared by the process describes in Examples III and IV above. Because of their radioactive nature, their syntheses was not undertaken.

The following analytical determinations were made for the europium and lanthanide complexes: Calcd for Eu($C_{16}H_{32}N_2O_5$)$Cl_3$: C, 32.53; H, 5.46; N, 4.74; Eu, 25.72. Found: C, 32.45; H, 5,60; N, 4.92; Eu, 24.73. Formation of the 2:2:2 cryptate salt was found to be more facile. The use of lanthanum nitrate yielded $(La(C_{18}H_{36}N_2O_6))(NO_3)_3$. Calcd: C, 30.79; H, 5.13. Found: C, 30.68; H, 5.15. These were the purest lanthanide compounds obtained by the process.

The lanthanide cryptates, particularly Eu(III) and Gd(III), exhibit remarkable kinetic stability in water and appear to be the first truly substitutionally inert complexes. Neutral solutions Eu $(2:2:1)^{3+}$ or Gd $(2:2:1)^{3+}$ show no metal hydroxide precipitate even after several days of aging. In strongly basic solution, pH 10, the complexes were stable for hours. No dissociation of complex was seen even after several days in 0.1 M aqueous perchloric acid as evidenced by unchanged NMR spectra. This inertness renders lanthanide cryptates particularly the $Gd(2:2:1)^{3+}$ ion useful as a $T_1$ (shiftless) relaxation reagent for nuclear magnetic resonance (NMR) spectroscopy in polar organic solvents or in aqueous solution. For $D_2O$ solutions containing 10% 1,4-dioxane and 40% acetone, successive additions of Gd $(2:2:1)^{3+}$ cryptate were seen, by using a Varian CFT-20 spectrometer, to reduce the $T_1$ relaxation times of the acetone $CH_3$ and CO carbons from 17.6 and 35.4 seconds, respectively, to 4.9 and 4.8 seconds at 0.0018 M Gd(III) and to 0.56 and 0.51 seconds at 0.018 M Gd(III). The relatively inert nature of the cryptate is proven by the exceedingly small (0.2, 1.1 Hz) paramagnetic shifts induced into these resonances, as measured vs. the dioxane signal, even at 0.18 M Gd(III) concentrations. Some very recent results of similarly decreased relaxation times metal nuclide NMR spectroscopy are even more portentous. The $T_1$ of Cd(II) is reduced from 20 sec. to 0.3 sec. by addition of 0.001 Molar $Gd(2:2:1)^{3+}$ to a 2.0 M solution of $Cd(ClO_4)_2$.

The effect of encryptation upon the electrochemical behavior of the Eu(III)/Eu(II) redox couple is also quite remarkable, as illustrated by the cyclic voltammograms shown in FIGS. 1 and 2. Sample waves observed for the reduction and subsequent reoxidation of aquated $Eu^{3+}$ ions in acidified 0.5 M $NaClO_4$ at a hanging mercury drop electrode are shown in FIGS. 1 and 2. The results are acid independent in the range of pH 1 to 4. The large and sweep rate dependent potential separation between the cathodic and anodic peaks arises from the irreversibility (i.e., slow heterogeneous electron transfer rates) of this couple. In contrast, the corresponding cyclic voltammograms shown in FIG. 2 for $Eu(2:2:1)Cl_3$ in 0.5 M $NaClO_4$ exhibit symmetrical peaks with a much smaller, sweep rate independent separation of 65 mV, which is close to the 57 mV value expected for electrochemically reversible redox couples at room temperature. A sizable (about 100 fold) catalysis of the Eu(III)/Eu(II) heterogeneous exchange reaction by encryptation is therefore indicated. Cryptate peak potentials were found to be pH independent in the range of pH 1 to 9 and were unchanged by the substitution of tetraethylamine perchlorate for sodium perchlorate at a given ionic strength. Taken together, these data provide strong evidence for the electrochemical and chemical reversibility of the $Eu(2:2:1)^{3+}/Eu(2:2:1)^{2+}$ couple and furthermore indicate that both species maintain their chemical integrity on the time scale of these measurements which indicates their usefulness as reducing agents for synthesis.

The differences in the voltammetric behavior between aquated and encryptated europium ions is useful for following the kinetics of the slow aquation of $Eu(2:2:1)^{3+}$. Thus, at pH 5, $Eu^{3+}(aq)$ is eventually formed as seen by the appearance of the normal, irreversible cyclic voltammograms and by the corresponding decrease in the magnitude of the cryptate peaks. Aquation rate constants, $k_{aq}$, for that Eu(III) species are measured to be slow, but pH dependent, being near $2\times10^{-4}$ per second at pH 12, $3\times10^{-7}$ per second at pH 7, and $1\times10^{-6}$ per second at pH 0 (for ionic strength of about 1). For the $Eu(2:2:1)^{2+}$ ion prepared by exhaustive cathodic electrolysis of the tripositive ion at a mercury pool electrode, markedly increased aquation rates (e.g., $2\times10^{-4}$ per second at pH 5) were observed.

The mean potential between the cathodic and anodic peaks in FIG. 2, $-435$ mV vs. SCE, can be approximately identified with the formal potential, Ef, for the $Eu(2:2:1)^{3+}/Eu(2:2:1)^{2+}$ couple. In contrast, Ef for $Eu^{3+}(aq)/Eu^{2+}(aq)$ has been determined to be $-625$ mV vs. SCE in 0.5 M $NaClO_4$. This positive shift of Ef upon encryption, $\Delta Ef = 190$ mV, is equal to $(2.303RT/F)(\log K_{11} - \log K_{111})$ where $K_{11}$ and $K_{111}$ are the stability constants for the formation of the Eu(II) and Eu(III) cryptates, respectively, leading to the result that $(\log K_{11} - \log K_{111}) = 3.2$. Two related Eu(III) cryptates, $Eu(2_B:2:1)^{3+}$ and $Eu(2:2:2)^{3+}$, have also been prepared and electrochemically characterized and yield similarly reversible cyclic voltammograms with even less negative values of Ef, $-370$ and $-225$ mV, which provide values of $(\log K_{11} - \log K_{111})$ of 4.3 and 6.8, respectively. A part of the explanation for the remarkably larger stabilities for Eu(II) vs. Eu(III) cryptates may be found in the significant expansion (~0.15Å) of the europium ionic radius upon reduction to the $+2$ state, yielding a better fit within the cryptate cavities. Another important factor may be the considerably greater desolvation that is required for encryptation of the more extensively aquated $Eu^{3+}$ ion.

A further surprising property of the $Eu^{3+}$ cryptates is their strong tendency to complex small anions. In the presence of fluoride or hydroxide anions, for example, cyclic voltammograms for $Eu(2:2:1)^{3+}$ are shifted without change of shape to markedly more negative potentials, and increasingly so when anion concentration is increased. By combining electrochemical data with that obtained from fluoride titration at a fluoride specific ion electrode, anion association with $Eu(2:2:1)^{3+}$ to form complexes containing both 2:2:1 or 2:2:2 ligands was detected, although no such ion association was found for $Eu(2:2:1)^{2+}$. Cumulative stability constants were found to be $3\times10^4$ per mole and $3\times10^6$ per mole, respectively, at an ionic strength $u=0.5$. These values are comparable with the corresponding stability constants for the association of aquated $Eu^{3+}$ with fluoride, $2.5\times10^3$ per mole and $3\times10^6$ per mole, respectively, at an ionic strength $u=0.5$. Similar behavior was found with the hydroxide ion. It is likely that these anions are present between the cryptate strands where they are able to closely approach the Eu(III) center and, because of their small size and negative charge, are able to compete effectively with water for those "coordination" sites.

Thus it can be seen that the metal cryptate compounds of the present invention are useful in electrochemistry, medicine and in synthetic techniques such as polymerization cryptands as described in German Offenlegundschrift No. 2,348,449.

We claim:

1. The process for forming a metal cryptate coordination compound which comprises:
    (a) refluxing an inorganic metal salt selected from lanthanide, actinide and first row divalent d-transition metal cations containing bound water in an anhydrous polar organic solvent selected from nitriles, ketones and esters with a dehydrating agent selected from trimethylorthoformate, triethylorthoformate and propylene carbonate dissolved in the solvent which reacts with the bound water to form an alcohol in situ thus removing the bound water and forming a product mixture containing a dehydrated metal salt;

(b) reacting the dehydrated metal salt in the product mixture of step (a) with a polyoxydiazamacrobicyclic polyether cryptand ligand; and (c) separating the encryptated metal salt from the solvent.

2. The process of claim 1 wherein the metal is a trivalent lanthanide series rare earth.

3. The process of claim 1 wherein the solvent is acetonitrile.

4. The process of claim 1 wherein the metal salt is a lanthanide series metal halide, nitrate or perchlorate.

5. The process of claim 1 wherein the separation is by precipitation of the encryptated metal salt.

6. The process of claim 5 wherein the precipitation is effected by adding an ether dropwise to the polar organic solvent.

7. The process of claim 1 wherein the cryptate ligand has the structural formula:

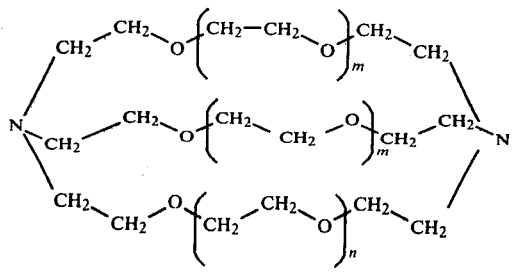

wherein m is 1 and n is 0 or wherein m and n are both 1 or of the structural formula:

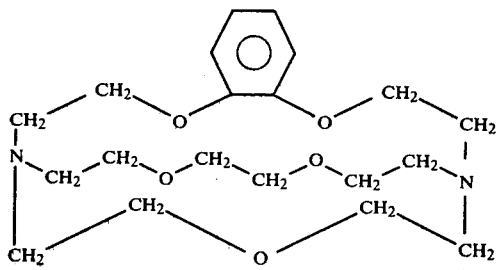

8. The process of claim 1 wherein refluxing is done under dry nitrogen.

* * * * *